United States Patent [19]

Iwamoto

[11] Patent Number: 4,738,533
[45] Date of Patent: Apr. 19, 1988

[54] PLYWOOD SURFACE DEFECT DETECTING HEAD

[75] Inventor: Yasuhiko Iwamoto, Ohbu, Japan

[73] Assignee: Meinan Machinery Works, Inc., Aichi, Japan

[21] Appl. No.: 792,682

[22] Filed: Oct. 29, 1985

[30] Foreign Application Priority Data

Oct. 30, 1984 [JP] Japan .................. 59-228759

[51] Int. Cl.⁴ ............................................. G01N 21/89
[52] U.S. Cl. ..................................... 356/237; 250/572
[58] Field of Search .............. 356/237, 239, 418, 430, 356/431; 250/227, 562, 572; 350/96.1

[56] References Cited

U.S. PATENT DOCUMENTS

| | | | |
|---|---|---|---|
| 3,120,861 | 2/1964 | Finlay et al. | 144/2 |
| 3,890,509 | 6/1975 | Maxey | 250/561 |
| 4,029,391 | 6/1977 | French | 356/418 X |
| 4,338,032 | 7/1982 | Bardsley et al. | 250/572 X |

FOREIGN PATENT DOCUMENTS 588531  1/1981  Japan .
0065147  4/1986  Japan .

OTHER PUBLICATIONS

IBM Technical Disclosure Bulletin, vol. 22, No. 10, Mar. 1980, "Detection of Underfilled Holes in a Ceramic Sheet".
Applied Optics, vol. 21, No. 19, Oct. 1, 1982, "Fiber-Optic Scattering Monitor for Use with Bulk Opaque Material".

*Primary Examiner*—Eugene R. LaRoche
*Assistant Examiner*—Robert J. Pascal
*Attorney, Agent, or Firm*—Lowe, Price, LeBlanc, Becker & Shur

[57] ABSTRACT

There is disclosed a plywood surface defect detecting head. It comprises a shielding plate slidingly contacted at its front end with one surface of the plywood, a light source provided at one side of the shielding plate, and an optical fiber provided at the other side of the shielding plate, the optical fiber being disposed such that one end thereof slidingly contacts the plywood surface together with the shielding plate and the other end thereof faces toward a light detector.

9 Claims, 3 Drawing Sheets

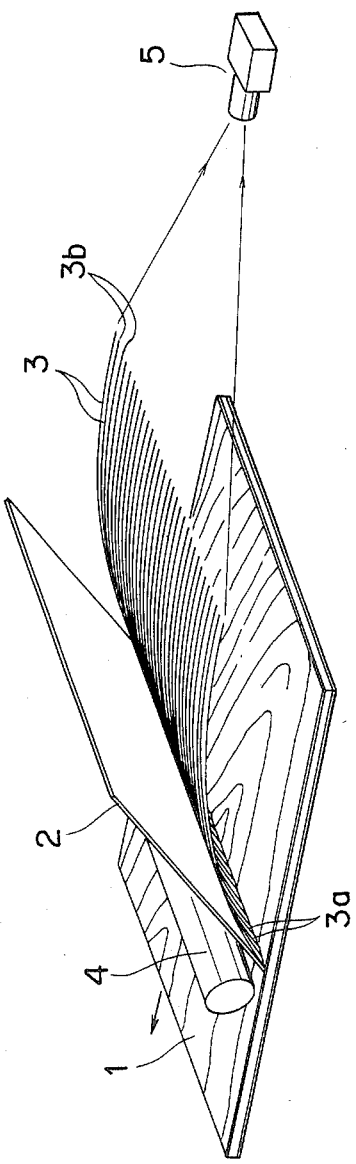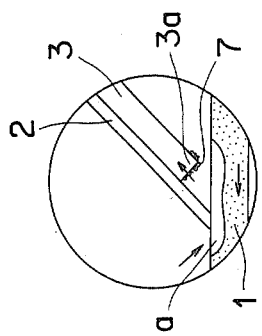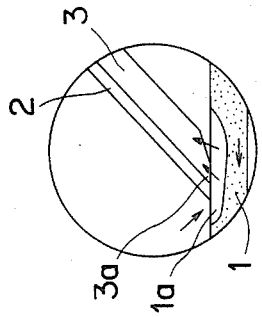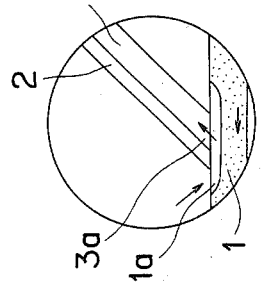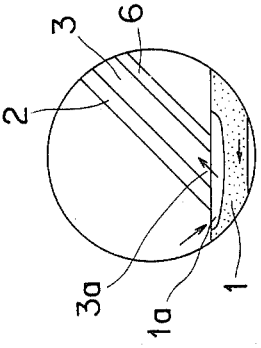

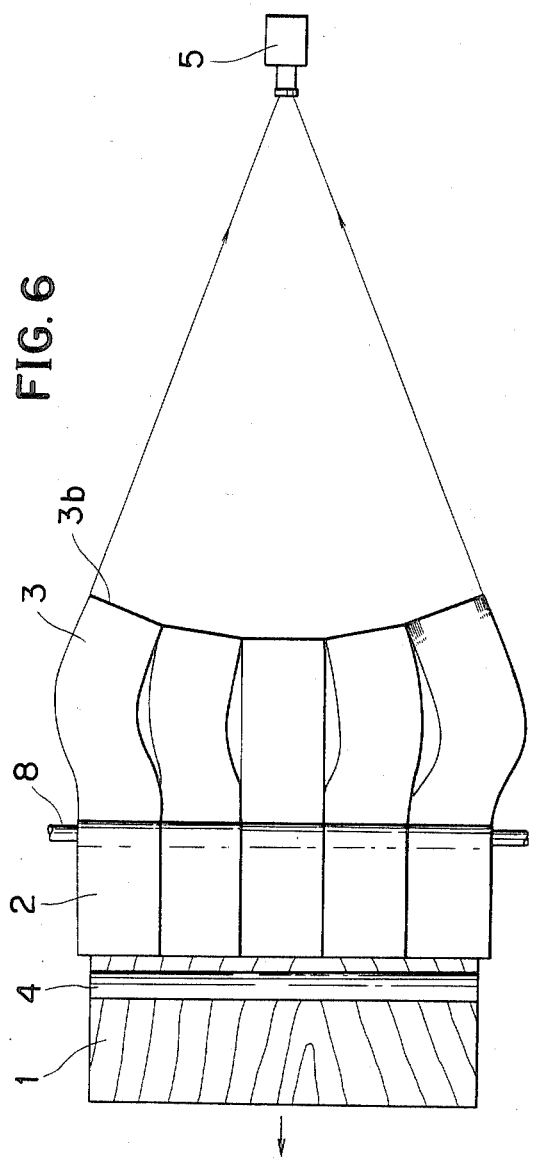
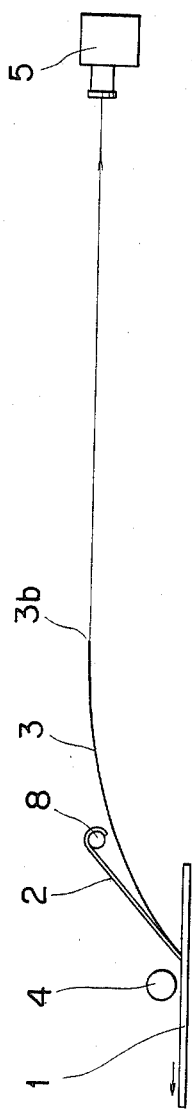

PLYWOOD SURFACE DEFECT DETECTING HEAD

BACKGROUND OF THE INVENTION

This invention relates to a plywood surface defect detecting head of the type used for detecting defects attributable to, for example, knot holes of original plates, worm holes, cracks, and the like, which exist in the surface of plywood.

In the above-mentioned field, it is an actual situation that the afore-mentioned type of defects are confirmed solely by sight of a worker. On the other hand, the applicant of the present invention has proposed in his prior Japanese Patent Application No. 59-188649 a detector for detecting concave-shaped defects in the surface of a plate-like member comprising a shielding member slidingly contacting the surface of a plate-like member at its front end, a moving mechanism for relatively moving the shielding member and the plate-like member, a light source disposed at one side of the shielding member, a number of light receiving elements disposed at the other side of the shielding member with required spaces according to capability of detection and resolution, and a control circuit for detecting the concave-shaped defects in the plate-like member based on light radiated toward the light receiving elements from the light source through a concave-shaped portion in the surface of the plate-like member when the shielding member is positioned in the concave-shaped portion according to the relative movement of the shielding member and the plate-like member.

When detection was carried out depending on a worker's sight, there existed such problems as unstable detection accuracy, poor working efficiency, high costs, etc.

Further, in the Japanese Patent Application No. 59-188649 set forth above, since its constitution is such that a number of light receiving elements are disposed at the other side of the shielding member, and the concave-shaped defects are detected by means of receipt of light passed through the concave-shaped defects by the respective light receiving elements, the light which has passed through the concave-shaped defects is often dispersed before it reaches the respective light receiving elements and enters in light receiving elements adjacent thereto. Accordingly, positions where the concave-shaped defects exist cannot be detected with high accuracy. In addition, light quantity is decreased due to the light dispersion. Because of the foregoing reasons, detection by the respective elements encountered difficulties.

The present invention was accomplished in order to overcome the problems inherent in the prior art.

SUMMARY OF THE INVENTION

It is therefore a general object of the present invention to provide an apparatus for detecting concave-shaped defects in the surface of plywood or a plate-like member, wherein concave-shaped defects can be highly resolved by preventing dispersion of light before it reaches a light detector such as a light receiving element, and can be stably detected for a long period of time.

In order to achieve the foregoing object, there is essentially provided a plywood surface defect detecting head comprising a shielding plate slidingly contacted at its front end with one surface of the plywood, a light source provided at one side of the shielding plate, and an optical fiber provided at the other side of the shielding plate, the optical fiber being disposed such that one end thereof slidingly contacts the plywood surface together with the shielding plate and the other end thereof faces toward a light detector.

According to the invention, the front end of a shielding plate and one end of an optical fiber both slidingly contact the surface of plywood according to the relative movement of a detecting head and the surface of the plywood. When concave-shaped defects existing in the surface of the plywood pass the shielding plate, light radiated from a light source passes the defects and immediately enters the optical fiber from one end thereof. And, the other end of the optical fiber projects the light toward the light detector.

BRIEF DESCRIPTION OF THE DRAWINGS

The present invention itself, together with other objects and advantages thereof will be best understood from the following detailed description of the illustrated embodiment when read in conjunction with the accompanying drawings, in which:

FIG. 1 is a perspective view of a plywood surface defect detecting head according to one preferred embodiment of the present invention;

FIG. 2 is an enlarged view showing part of FIG. 1 which is material to the invention;

FIG. 3 is likewise an enlarged view similar to FIG. 2 but showing a modified embodiment in which one end of an optical fiber is not in sliding contact with the surface of a plywood;

FIG. 4 is likewise an enlarged view similar to FIG. 2, but showing another modified embodiment in which a wear control plate is added to FIG. 2;

FIG. 5 is likewise an enlarged view similar to FIG. 2 but showing one undesirable example only for explanation purpose;

FIG. 6 is a schematic plan view in which the present invention is applied to plywood having a wide width;

FIG. 7 is a side view of FIG. 6;

DETAILED DESCRIPTION OF THE EMBODIMENTS

Figure 8:
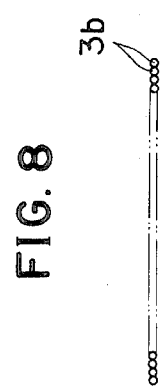
FIG. 8 is a front view showing one end portion of an optical fiber.

In FIG. 1, 1 denotes a plywood movable in the direction as shown by an arrow, 2 denotes a shielding plate, 4 denotes a light source, and 3 denotes an optical fiber. In this embodiment, the optical fiber 3 has 31 fibers. Constitution of the embodiment is such that concave-shaped defects (not shown) can be detected at desired spaces throughout the whole width of the plywood 1. 5 denotes an optical detector having a CCD image sensor. There can be used as such sensor, for example, VIDEO MEASURE (merchandise name) manufactured by Tateishi Denki Kabushiki Kaisha. Also, there can be used as the optical fiber both of a glass system and a plastic system. In this embodiment, the cheap priced plastic system can serve the purpose. For example, ESKA (merchandise name) manufactured by Mitsubishi Rayon Kabushiki Kaisha can be used for it. When many fibers are used as the present case is, it is convenient to use ESKA OPTICAL SHEET (merchandise name). On the other hand, a metallic leaf spring is suitable for the shielding plate 2. The thickness of the sliding portion thereof is determined based on the minimum dimension of a concave-shaped defect to be detected. From a view point of general use, it is preferably formed of a leaf spring having a thickness of about 0.1 to 4 mm in order to manufacture it at a low cost. Of course, the shielding plate 2 is not limited to metal. Instead, there may be used such materials as plastics, rubbers, and the like. Preferably, the front end of the plate 2 slidingly contacting the plywood 1 should be formed of an elastic material so that it can be deformed according to undulations (waviness) of the surface of the plywood 1.

FIG. 2 illustrates an enlarged view of part of FIG. 1. In the figure, 1a denotes a concave-shaped defect of the plywood 1, and light emitted from a light source (not shown, but the radiating direction of the light is shown by an arrow) provided at the left side of the shielding plate 2 passes through the defect 1a and enters in an optical fiber 3 from one end 3a thereof. Supposing the defect 1a is a worm hole existing in an original plate of the plywood 1, among 31 optical fibers 3 in FIG. 1, only a fiber having one end at an upper location of the defect 1a projects a strong light toward a light detector 5 from the other end 3b thereof. The detector 5 detects and treats the concave-shaped defect 1a due to the worm hole according to the difference of light and shade between the fore-mentioned other end 3b and the other ends of the remaining optical fibers. With respect to convex-shaped defects where original plates are partly overlapped, the defects can also be detected in the same manner as the concave-shaped defects by detecting light passed through one side or both sides of the defects.

FIG. 3 illustrates one example of the optical fiber 3, wherein a part of one end 3a of the fiber 3 is not in sliding contact with the surface of the plywood 1. Even in this case, since the remaining part is in sliding contact with the surface, it is also included in the present embodiment. In this example, both the shielding plate 2 and the optical fiber 3 are in sliding contact with the surface of the plywood 1. Accordingly, they are gradually worn and enter a condition shown in FIG. 3.

Also, FIG. 4 illustrates one example wherein the example of FIG. 2 is added with a wear adjusting plate 6 which slidingly contacts the surface of the plywood 1 moving in the direction as shown by an arrow, together with the shielding plate 2 and the optical fiber 3. The addition of the plate 6 minimizes wear of the optical fiber 3 and adjustment therefor.

FIG. 5 illustrates an optical fiber 3 which is not an embodiment of the present invention, and one end 3a of which is disposed in a manner spaced apart from the surface of the plywood. In this case, dust 7 such as wood powder and sander powder attaches to one end 3a of optical fiber 3, which decreases incident efficacy of the light. Moreover, the light passed through the concave-shaped defect 1a is dispersed and thereafter enters the optical fiber 3 from one end 3a thereof. Accordingly, since the light also enters the remaining optical fibers adjacent thereto, capability of detection and resolve is decreased extensively.

FIGS. 6 and 7 illustrate in a shape of a plan view and a front view an example of a plywood having a wide width to which the present invention is applied. As apparent from the figures, in this example, the whole width of the plywood 1 is divided into five portions, and five shielding plates 2 are pivotally disposed on a support shaft 8, so that the front end thereof can more flexibly follow the undulation of the plywood 1. Moreover, the optical fiber 3 is formed of a number of fibers formed in a sheet-shape of dense linear fibers which are integrally attached to the front end portions of the respective shielding plates 2. The other ends 3b for projecting the light toward the light detector are bent per each unit, as shown in the figures. In this way, when one including a lens optical system is employed as the light detector, objective distance can be adjusted according to necessity to obtain a favorable focusing.

The optical fiber 3 is disposed with the other end 3b facing the light detector 5 as shown in FIG. 8. Every time the concave-shaped defect passes, some of the number of optical fibers project a strong light, thereby enabling to detect the defect, its size, and its position.

Figure 11:
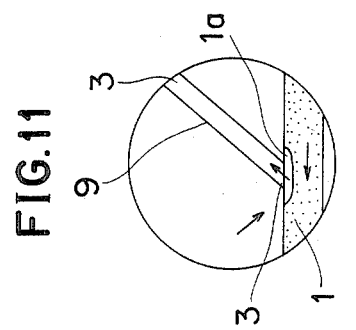
FIGS. 9 through 11 are enlarged views similar to FIG. 2 but showing still further modified embodiments thereof.
Figure 10:
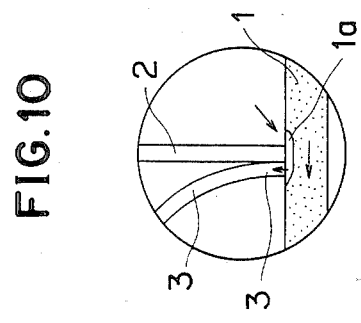
Figure 9:
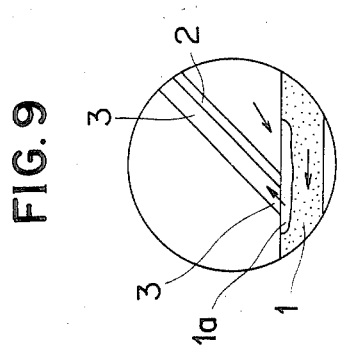

FIGS. 9 through 11 illustrate modified embodiments relating to disposition of shielding plate 2, optical fiber 3, and the light source. In the embodiment shown in FIG. 9, with respect to the progressing direction as shown by an arrow of the plywood 1, disposed at the initial position are a light source, then shielding plate 2, and optical fiber 3 in this order. Similarly, in the embodiment shown in FIG. 10, anglewise alternation is applied. If necessary, the emboidment in FIGS. 2 through 4 may be constituted by reversing the progressing direction of plywood 1. Also, as shown in FIG. 11, at least at the light source side a coating film may be formed, or otherwise various kinds of plastic resins may be attached thinly to form substantial shielding plate 9.

Regarding the light detector, there are well known detectors other than the one shown by way of example. They can be selectively used according to necessity. Depending on what type of detector is used, the other end 3b of the optical fiber can be suitably optically connected to the light detector.

As described in the foregoing, the present invention is simple in its constitution, and yet can detect a defect existing in the surface of plywood without dispersing the light passed through the defect. Accordingly, an extremely satisfactory detection can be obtained. In addition, since one end of the optical fiber is in sliding contact with the surface of the plywood, attachment of dusts or the like is very few. Thus, a satisfactory wear surface (which corresponds to the grinding surface since the object is wood) can be always maintained, and an extremely favorable transmission efficiency can be obtained. Accordingly, this invention will be sure to contribute to automation of detection of a defect in inspection process, filling treatment process, etc. of plywood, and also to the plywood industry.

Although the present invention has been fully described by way of example with reference to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A plywood surface defect detecting head for detecting defects in a surface of plywood, comprising:
   a shielding plate having a front end extending laterally with respect to a path of plywood fed in a predetermined direction, said front end slidingly contacting with said surface of the plywood;

a light source provided at one side of said shielding plate; and at least one optical fiber provided at the other side of said shielding plate, said optical fiber being disposed such that one end thereof slidingly contacts the plywood surface together with said shielding plate front edge and the other end thereof faces toward a light detector.

2. A plywood surface defect detecting head according to claim 1, wherein said shielding plate is attached at its front end portion with said one end of said optical fiber.

3. The detecting head of claim 1, further including a wear adjusting plate mounted so that said one end of the optical fiber is disposed between the shielding plate and the wear adjusting plate.

4. The detecting head of claim 1, wherein said front end of the shielding plate and said one end of the optical fiber are formed obliquely with respect to the surfces between which these ends extend.

5. The detecting head of claim 1, further comprising a plurality of said optical fibers secured to the front end of the shielding plate to extend along the width of the plate.

6. The detecting head of claim 1, further including a plurality of shielding plates pivotally mounting at rear ends thereof to a support shaft.

7. A detecting head for detecting defects in a surface of plywood which is being transferred, said detecting head comprising:

a shielding plate having a linear edge and extending laterally with respect to a path of plywood fed in a predetermined direction and slidingly contacting said plywood at said linear edge;

a light source provided on a first side of said shielding plate; and a row of optical fibers arranged on a second side of said shielding plate, each optial fiber being disposed such that one end thereof slidingly contacts the plywood surface along said linear edge of the shielding plate.

8. A detecting head for detecting defects in a surface of plywood according to claim 7, wherein said first side of the shielding plate is downstream of the shielding plate and said second side of the shielding plate is upstream of said shielding plate.

9. A detecting head for detecting defects in a surface of plywood according to claim 8, wherein said shielding plate is inclined toward the upstream side.

* * * * *